US012208262B2

(12) United States Patent
Wasserman

(10) Patent No.: US 12,208,262 B2
(45) Date of Patent: Jan. 28, 2025

(54) OPTIMIZATION OF COMPOSITE ELECTRODE

(71) Applicant: Novocure GmbH, Root (CH)

(72) Inventor: Yoram Wasserman, Haifa (IL)

(73) Assignee: Novocure GmbH (CH)

( * ) Notice: Subject to any disclaimer, the term of this patent is extended or adjusted under 35 U.S.C. 154(b) by 0 days.

(21) Appl. No.: 18/528,168

(22) Filed: Dec. 4, 2023

(65) Prior Publication Data
US 2024/0108889 A1    Apr. 4, 2024

Related U.S. Application Data

(63) Continuation of application No. 17/550,423, filed on Dec. 14, 2021.

(60) Provisional application No. 63/128,265, filed on Dec. 21, 2020.

(51) Int. Cl.
*A61N 1/32* (2006.01)
*A61B 18/14* (2006.01)
*A61N 1/20* (2006.01)

(52) U.S. Cl.
CPC .......... *A61N 1/326* (2013.01); *A61N 1/205* (2013.01); *A61B 2018/147* (2013.01)

(58) Field of Classification Search
CPC ...... A61N 1/326; A61N 1/205; A61N 1/0456; A61N 1/36002; A61N 1/3603; A61N 1/0476; A61B 2018/147
See application file for complete search history.

(56) References Cited

U.S. PATENT DOCUMENTS

| | | |
|---|---|---|
| 2017/0281934 A1 | 10/2017 | Biladi et al. |
| 2018/0050200 A1 | 2/2018 | Wasserman et al. |
| 2020/0155835 A1 | 5/2020 | Wasserman et al. |
| 2020/0269043 A1 | 8/2020 | Wasserman et al. |

OTHER PUBLICATIONS

International Search Report and Written Opinion (PCT/IB2021/061711), dated Mar. 14, 2022, 13 pages.

*Primary Examiner* — Mallika D Fairchild
(74) *Attorney, Agent, or Firm* — Dunlap Codding, P.C.

(57) ABSTRACT

Apparatuses and methods for imposing electric fields through a target region a patient are described. An apparatus includes a transducer array having a first and second electrode element receiving an alternating current waveform and a sensor array having a first temperature sensor positioned to detect a first temperature of the first electrode element and a second temperature sensor positioned to detect a second temperature of the second electrode element. The first temperature sensor is connected to a first conductor and second conductor. The second temperature sensor is connected to the second conductor and third conductor. A circuit provides a first known amount of electricity via the first conductor and second conductor to obtain the first temperature and a second known amount of electricity via the second conductor and the third conductor to obtain the second temperature. A controller adjusts the alternating current waveform based on the temperatures.

16 Claims, 5 Drawing Sheets

OPTIMIZATION OF COMPOSITE ELECTRODE

CROSS-REFERENCE TO RELATED APPLICATIONS

This application is a continuation application of U.S. patent application Ser. No. 17/550,423, filed Dec. 14, 2021, which claims priority to U.S. Provisional Application No. 63/128,265, filed Dec. 21, 2020, the entire contents of which are hereby expressly incorporated herein by reference in their entirety.

STATEMENT REGARDING FEDERALLY SPONSORED RESEARCH

Not Applicable.

BACKGROUND OF THE ART

Tumor Treating Fields (TTFields or TTFs) are low intensity (e.g., 1-3 V/cm) alternating electric fields within the intermediate frequency range (100-500 kHz) that target solid tumors by disrupting mitosis. This non-invasive treatment targets solid tumors and is described, for example, in U.S. Pat. Nos. 7,016,725; 7,089,054; 7,333,852; 7,565,205; 8,244,345; 8,715,203; 8,764,675; 10,188,851; and 10,441,776. TTFields are typically delivered through two pairs of transducer arrays that generate perpendicular fields within the treated tumor; the transducer arrays that make up each of these pairs are positioned on opposite sides of the body part that is being treated. More specifically, for the OPTUNE® system, one pair of electrodes of the transducer arrays is located to the left and right (LR) of the tumor, and the other pair of electrodes is located anterior and posterior (AP) to the tumor. TTFields are approved for the treatment of glioblastoma multiforme (GBM), and may be delivered, for example, via the OPTUNE® system (Novocure Limited, St. Helier, Jersey), which includes transducer arrays placed on the patient's shaved head.

Each transducer array used for the delivery of TTFields in the OPTUNE® device comprises a set of non-conductive ceramic disk electrodes, which are coupled to the patient's skin (such as, but not limited to, the patient's shaved head for treatment of GBM) through a layer of conductive medical gel. To form the ceramic disk electrodes, a conductive layer is formed on a top surface of nonconductive ceramic material. A bottom surface of the nonconductive ceramic material is coupled to the conductive medical gel. The nonconductive ceramic material is a safety feature to ensure that direct-current signals are blocked from unintentionally being transmitted to the patient by mistake. By interposing a nonconductive ceramic material between the conductive layer and the conductive medical gel, the prior art system was thought to ensure the patient remains protected. The purpose of the medical gel is to deform to match the body's contours and to provide good electrical contact between the arrays and the skin; as such, the gel interface bridges the skin and reduces interference. The device is intended to be continuously worn by the patient for 2-4 days before removal for hygienic care and re-shaving (if necessary), followed by reapplication with a new set of arrays. As such, the medical gel remains in substantially continuous contact with an area of the patient's skin for a period of 2-4 days at a time, and there is only a brief period of time in which the area of skin is uncovered and exposed to the environment before more medical gel is applied thereto.

One approach to applying the TTField in different directions is to apply the field between a first set of electrodes for a period of time, then applying a field between a second set of electrodes for a period of time, then repeating that cycle for an extended duration (e.g., over a period of days or weeks).

In order to generate the TTFields, current is applied to each electrode of the transducer array. The application of current over a period of time causes each electrode to warm and eventually become hot, and thus uncomfortable or painful to the patient. As such, the amplitude of the alternating current that is delivered via the transducer arrays may be controlled so that skin temperature (as measured on the skin below the transducer arrays) does not exceed a safety threshold (e.g., 41 degrees Celsius, for example). The temperature measurements on the patient's skin are obtained using temperature sensors (e.g., thermistors) placed beneath some of the disks of the transducer arrays. For example, each array may include eight thermistors, with one thermistor positioned beneath a respective disk in the array.

The thermistors in each array are connected via long wires to an electronic device called the "cable box" where the temperature from all thermistors (e.g., four arrays×eight thermistors per array) is measured and analog-to-digital converted into digital values for each thermistor. These measurements are then transmitted from the cable box to the field generator via additional wire(s) that facilitate two-way digital serial communications between the cable box and the field generator. The controller in the field generator uses the temperature measurements to control the current to be delivered via each pair of arrays in order to maintain temperatures below, for example, 41 degrees Celsius on the patient's skin. The current itself is delivered to each array via an additional wire (i.e., one wire for each array) that runs from the field generator through the cable box to the array.

Attaching temperature sensors and transducer arrays to a patient is cumbersome with the amount of wires. As such, new and improved array assemblies that reduce the number of wires may reduce cost and increase patient comfort. It is to such assemblies and methods of producing and using the same, that the present disclosure is directed.

DETAILED DESCRIPTION

Figure 1:
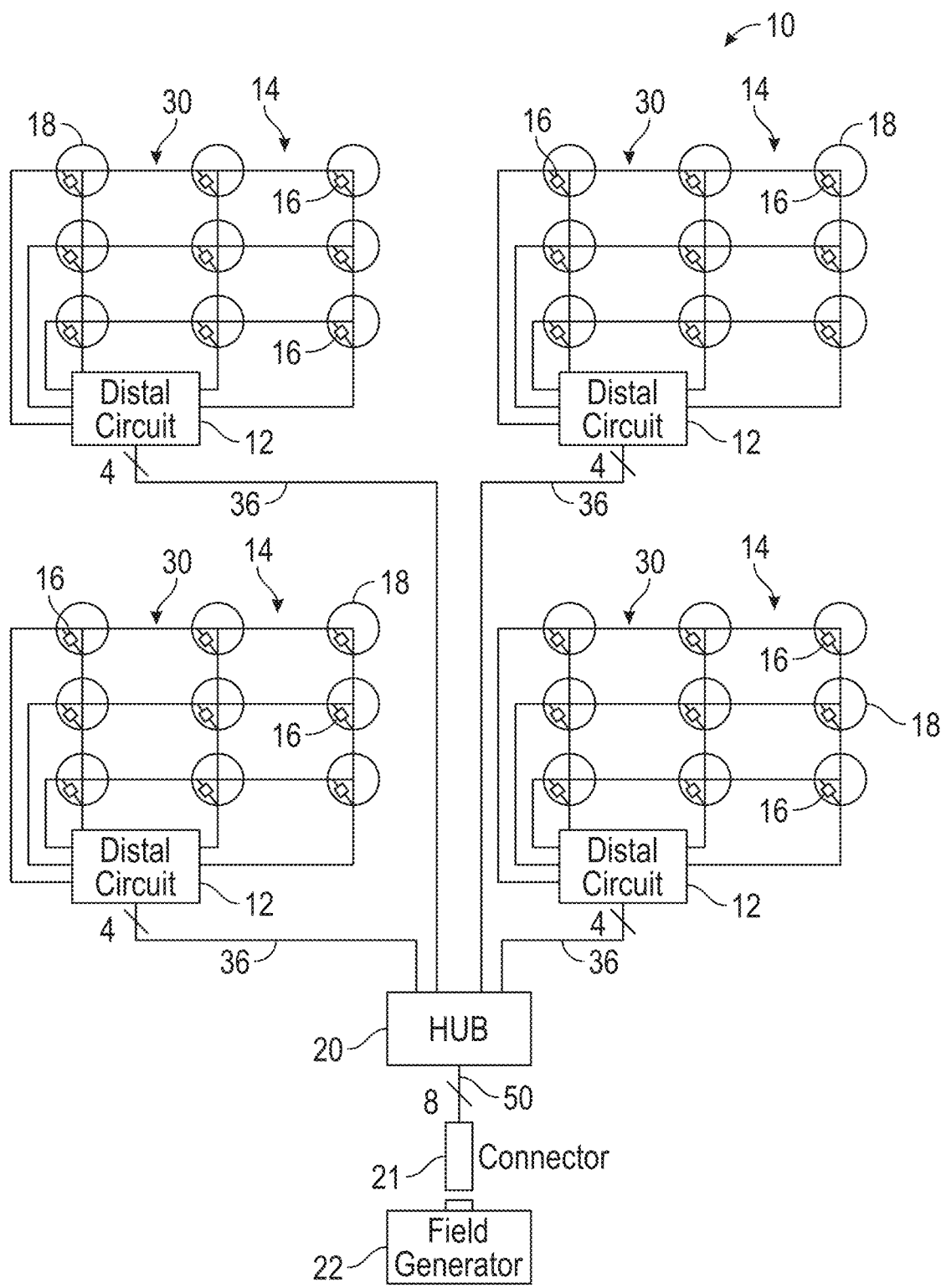
FIG. 1 is a block diagram of an exemplary system for measuring the temperature of transducer arrays applying TTFields to a body of a patient in accordance with the present disclosure.

Before explaining at least one embodiment of the inventive concept(s) in detail by way of exemplary language and results, it is to be understood that the inventive concept(s) is not limited in its application to the details of construction and the arrangement of the components set forth in the following description. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification.

All patents, published patent applications, and non-patent publications mentioned in the specification are indicative of the level of skill of those skilled in the art to which this presently disclosed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the assemblies, systems, kits, and/or methods disclosed herein can be made and executed without undue experimentation in light of the present disclosure. While the assemblies, systems, kits, and methods of the inventive concept(s) have been described in terms of particular embodiments, it will be apparent to those of skill in the art that variations may be applied to the compositions and/or methods and in the steps or in the sequence of steps of the methods described herein without departing from the concept, spirit, and scope of the inventive concept(s). All such similar substitutions and modifications apparent to those skilled in the art are deemed to be within the spirit, scope, and concept of the inventive concept(s) as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for an apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. For example, the term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

The term "patient" as used herein includes human and veterinary subjects. "Mammal" for purposes of treatment refers to any animal classified as a mammal, including (but not limited to) humans, domestic and farm animals, nonhuman primates, and any other animal that has mammary tissue.

The term "treatment" refers to both therapeutic treatment and prophylactic or preventative measures. Those in need of treatment include, but are not limited to, individuals already having a particular condition/disease/infection as well as individuals who are at risk of acquiring a particular condition/disease/infection (e.g., those needing prophylactic/preventative measures). The term "treating" refers to administering an agent/element/method to a patient for therapeutic and/or prophylactic/preventative purposes.

Administering a therapeutically effective amount or prophylactically effective amount is intended to provide a therapeutic benefit in the treatment, prevention, and/or management of a disease, condition, and/or infection. The specific amount that is therapeutically effective can be readily determined by the ordinary medical practitioner, and can vary depending on factors known in the art, such as (but not limited to) the type of condition/disease/infection, the patient's history and age, the stage of the condition/disease/infection, and the co-administration of other agents.

The term "effective amount" refers to an amount of a biologically active molecule or conjugate or derivative thereof, or an amount of a treatment protocol (i.e., an alternating electric field), sufficient to exhibit a detectable therapeutic effect without undue adverse side effects (such as (but not limited to) toxicity, electrolysis, irritation, and allergic response) commensurate with a reasonable benefit/risk ratio when used in the manner of the inventive concept (s). The therapeutic effect may include, for example but not by way of limitation, preventing, inhibiting, or reducing the occurrence of at least one tumor and/or cancer. The effective amount for a subject will depend upon the type of subject, the subject's size and health, the nature and severity of the condition/disease/infection to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

Circuitry, as used herein, may be analog and/or digital components, or one or more suitably programmed processors (e.g., microprocessors) and associated hardware and software, or hardwired logic. Also, "components" may perform one or more functions. The term "component," may include hardware, such as a processor (e.g., microprocessor), an application specific integrated circuit (ASIC), a field programmable gate array (FPGA), a combination of hardware and software, and/or the like. The term "processor" as used herein means a single processor or multiple processors working independently or together to collectively perform a task.

Turning now to the inventive concept(s), certain non-limiting embodiments thereof include a system and method of implementing the system, the system comprising a generator configured to generate an electrical signal having an alternating current waveform at a frequency in a range from fifty kHz to five hundred kHz; a first conductive lead electrically coupled to the generator, the first conductive lead configured to carry the electrical signal; a first pad having a first electrode element electrically coupled to a first conductive gel element to supply electrical current to the first conductive gel element, the first electrode element having an electrode layer and a non-conductive flexible polymer layer, wherein the first electrode element is electrically coupled to the first conductive lead, and the first conductive gel element is configured to be in contact with a patient's skin; and a second pad having a second electrode element electrically coupled to a second conductive gel element to supply electrical current to the second conductive gel element, wherein the second electrode element is electrically coupled to the second conductive lead, and the second conductive gel element is configured to be in contact with a patient's skin.

Figure 2:
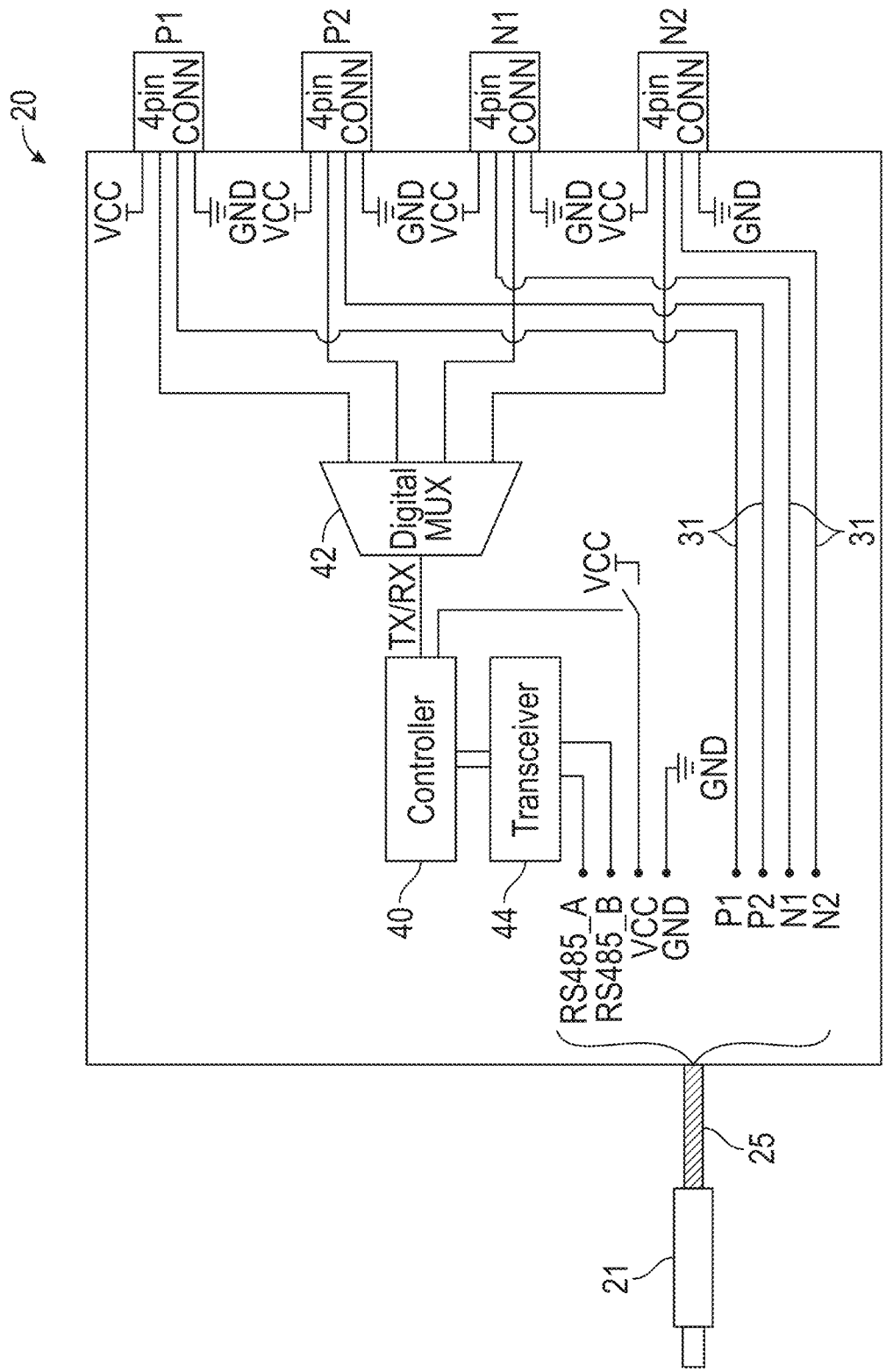
FIG. 2 is a schematic diagram of an exemplary hub for use in the system illustrated in FIG. 1 in accordance with the present disclosure.

Referring now to the drawings, and in particular FIGS. 1 and 2, shown therein are block diagrams of an exemplary embodiment of a system 10 having one or more distal circuits 12 positioned in close proximity to one or more transducer arrays 14 to obtain one or more temperature readings from one or more temperature sensors 16. Each of the transducer arrays 14 includes one or more electrode elements 18. Alternative constructions for the transducer arrays 14 may also be used, including, for example, transducer arrays using ceramic elements that are not disc-shaped, and/or transducer arrays that use non-ceramic dielectric materials positioned over a plurality of flat conductors. Examples of the latter include polymer films disposed over pads on a printed circuit board or over flat pieces of metal. Transducer arrays that use electrode elements that are not capacitively coupled may also be used. In this situation, each element of the transducer array may be implemented using a region of a conductive material that is configured for placement against a person's body, with no insulating dielectric layer disposed between the conductive elements and the body. Examples of the conductive material include, but are not limited to, a conductive film, a conductive fabric, and/or a conductive foam. Other alternative constructions for implementing the transducer arrays may also be used, as long as they are (a) capable of delivering TTFields to the person's body and (b) utilize the improved connector designs described herein positioned in the locations specified herein. Optionally, a layer of hydrogel may be disposed between the transducer arrays and a body of a person in any of the embodiments described herein.

The one or more temperature sensors 16 are positioned to detect the temperature at the electrode elements 18. In some embodiments, the temperature sensors 16 may be thermistors, thermocouples, RTDs, integrated circuit temperature sensors such as the Analog Devices AD590 and the Texas Instruments LM135, and/or combinations thereof.

Each distal circuit 12 interfaces with the one or more temperature sensors 16 that are incorporated into the respective transducer array 14 to obtain temperature readings from each of the one or more temperature sensor 16. The distal circuit 12 then may convert (e.g., analog to digital) the temperature readings, forward the temperature reading and/or send the temperature readings to a hub 20. The hub 20 may then forward the temperature reading and/or send the temperature readings to a field generator 22 (e.g., via a serial communication link). In some embodiments, the field generator 22 may determine, based on the temperature readings, adjustment of the current to the transducer arrays 14.

In some embodiments, conductors 30 may extend distally beyond the distal circuit 12 into the transducer array 14. Each temperature sensor 16 may be connected to at least two conductors 30 such that selective activation of the at least two conductors 30 may activate the temperature sensor 16 to obtain one or more temperature readings (e.g., selective activation on a time basis).

Additionally wiring extending from the distal circuit 12 may include but is not limited to, one or more conductors for the one or more temperature sensors' common ground, and one or more conductors for the TTFields signal (i.e., the AC current for the electrode elements), and the like. In some embodiments, the distal circuit 12 may be implemented using a single-chip microcontroller or Programmable System on Chip (PSoC) with a built in analog front end and multiplexer. Suitable part numbers for this purpose include the CY8C4124LQI-443, manufactured by Cypress Semiconductor Corp., having a principal place of business in San Jose, California.

As one skilled in the art will appreciate, some embodiments may include one or more microcontrollers having built-in and/or discrete analog front ends and/or multiplexers. For example, the analog front end and multiplexer may obtain temperature readings from the one or more temperature sensors 16. Those temperature readings may then be digitized and/or transmitted to the hub 20, (e.g., via serial data link). In some embodiments, each distal circuit 12 may also include one or more pass-through conductors 34 (see FIG. 3). The one or more pass-through conductors 34 may be configured to route one or more TTFields signal that originated in the field generator 22 to the transducer array 14.

In some embodiments, each distal circuit 12 may be connected to the hub 20 via one or more cable 36. Conductors 34 in each cable 36 may run between the distal circuit 12 and the hub 20. For example, in FIG. 3, four conductors 34 run between each distal circuit 12 and the hub 20, including, one conductor 34 for power ($V_{CC}$), one conductor 34 for grounding (GND), one conductor for serial data communication (DATA), and one for the TTF signal.

Generally, the hub 20 may receive one or more temperature readings from each of the distal circuits 12 and may send the one or more temperature readings to the field generator 22. Any of a wide variety of architectures may be used to receive and send the one or more temperature readings. For example, FIG. 2 illustrates a controller 40 configured to send a signal to a digital multiplexer 42 that commands the digital multiplexer 42 to select one of the distal circuits 12 such that the hub 20 may receive digital data from the distal circuit 12 (e.g., the first distal circuit 12).

The controller 40 receives the one or more temperature readings from the selected input of the distal circuit 12 and transmits the one or more temperature readings to the field generator 22 via the transceiver 44. The controller 40 may then update the control signal to the digital multiplexer 42 such that the digital multiplexer 42 selects another distal circuit 12 (e.g., the second distal circuit 12). The controller 40 then receives one or more temperature readings from the input of the second distal circuit 12 and transmits one or more temperature readings to the field generator 22. Corresponding sequences may be then performed to obtain suitable temperature readings (e.g., nine temperature readings) from each of the distal circuits 12. In some embodiments, the entire sequence of obtaining each of the one or more temperature readings from each of the distal circuits 12 or a portion of the sequence may be repeated periodically (e.g., every 1/100 second, 1 second, 10 seconds, or 30 seconds) to update the one or more temperature readings that are provided to the field generator 22.

In some embodiments, the controller 40, the digital multiplexer 42, and/or the transceiver 44 may be integrated together into a single chip. In some embodiments, the controller 40 and the digital multiplexer 42 may be integrated together into circuitry including a single chip, and a separate transceiver 44 is used. For example, the controller 40 and the digital multiplexer 42 may be implemented using a Cypress CY8C4244LQI-443, manufactured by Cypress Semiconductor Corp., having a principal place of business in San Jose, California, and the transceiver 44 may be implemented using a Linear Technology LTC2856CMS8-2 #PBF, manufactured by Linear Technology Corp., having a principal place of business in Milpitas, California. The controller 40 and/or the digital multiplexer 42 may be implemented as a processor executing software to perform the functions described herein.

The hub 20 may communicate with the field generator 22 using any conventional communication technique (e.g., RS485). In some embodiments, the hub 20 may include one or more pass-through conductors configured to pass one or more TTField signals directly from the field generator 22 to each of the transducer arrays 14. In some embodiments, the hub 20 may communicate with the field generator 22 via an 8-conductor spiral cable 50. For example, the hub 20 may communicate with the field generator 22 via an 8-conductor spiral cable wherein four wires may provide for TTFields signals from each transducer array 14, one wire may provide for ground (GND), one wire may provide for voltage (Vcc) to the distal circuits 12, and two wires may provide for communication (RS485A and RS485B). It should be noted that use of 8-conductor spiral cable 50 is configured to be backwards compatible with prior versions of TTField delivery systems within the art as one skilled in the art will appreciate.

Communication wires may be configured to implement data communications between the hub 20 and the field generator 22 (i.e., for the temperature data). In some embodiments, one wire may be configured to implement communication in each direction. In some embodiments, wire count between the hub 20 and the field generator 22 can be reduced by replacing multiple data communication wires with a single data wire that implements two-way communication (using a conventional single wire communication protocol).

Figure 3:
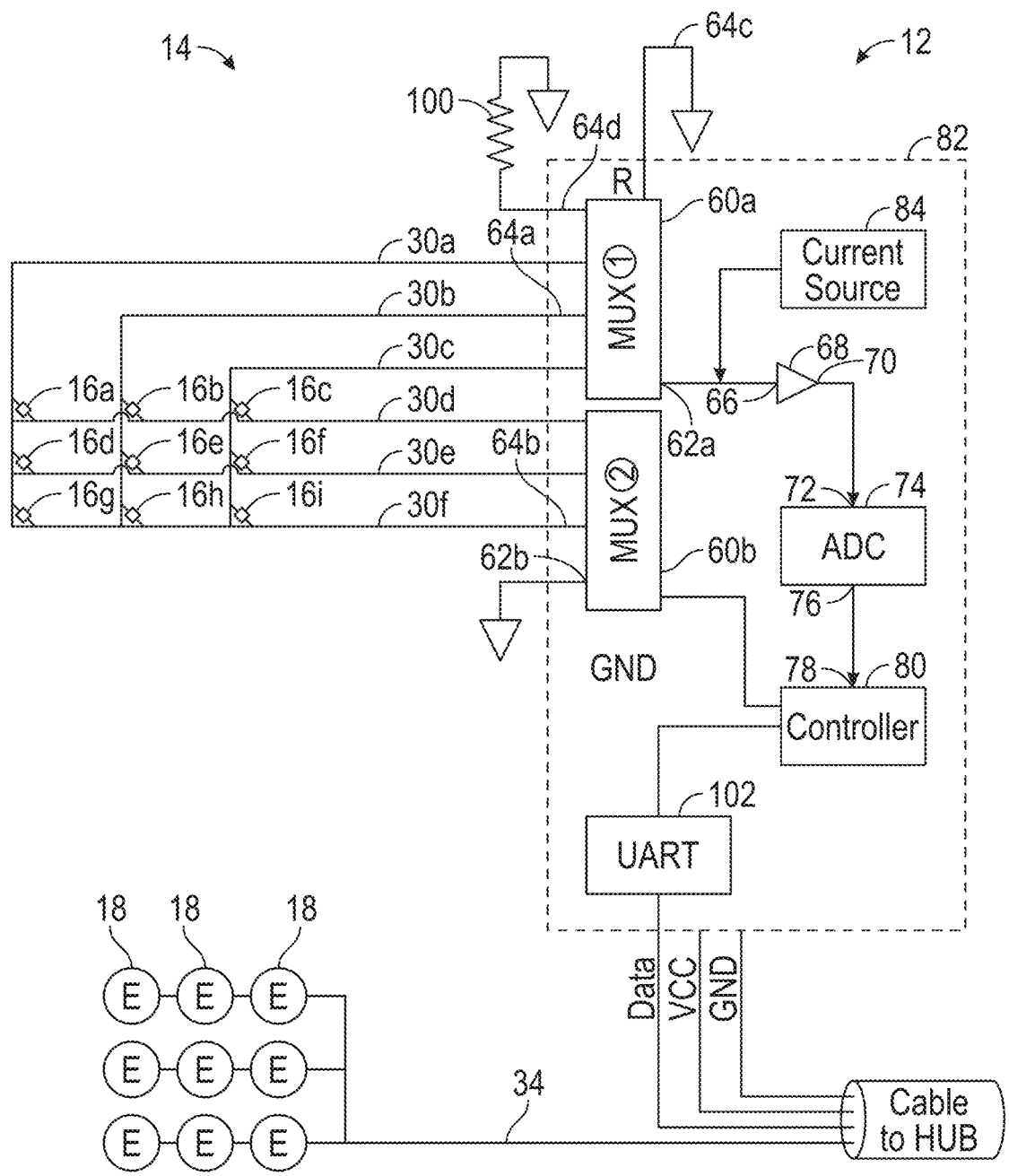
FIG. 3 is a schematic diagram of an exemplary distal circuit for use in the system illustrated in FIG. 1 in accordance with the present disclosure.

FIG. 3 is a schematic diagram of an exemplary distal circuit 12 for interfacing the hub 20 with the one or more transducer array 14. Each transducer array 14 may include one or more electrode elements 18 and one or more temperature sensors 16 positioned to sense temperatures of the one or more electrode elements 18. The one or more temperature sensors 16 may include, but are not limited to, thermistors, thermocouples, RTDs, integrated circuit temperature sensors such as the Analog Devices AD590 and the Texas Instruments LM135, and/or combinations thereof. It is contemplated that any temperature sensor 16 known within the art may be used if configured to provide an accurate and/or precise temperature reading in accordance with the present disclosure. In some embodiments, one or more temperature sensors 16 may be thermistors.

The distal circuit 12 may include a first multiplexer 60a and a second multiplexer 60b. Generally, the first multiplexer 60a drives a known amount of electricity (e.g., current) to the one or more temperature sensor 16 and the second multiplexer 60b electrically connects one or more temperature sensor 16 to a reference point (e.g., GND).

The first multiplexer 60a includes an output 62a and one or more selectable inputs 64a. Each of the one or more selectable inputs 64a may be connected to two or more temperature sensors 16. To that end, each temperature sensor 16 may be connected to at least two conductors 30. At least one terminal 64c may be a common ground. In some embodiments, the output 62a of the first multiplexer 60a may be provided to an input 66 of an amplifier 68, (e.g., amplifier having a high input impedance such as an op amp configured as a voltage follower). Output 70 of the amplifier 68 may be provided to an input 72 of an analog to digital converter 74. Output 76 of the analog to digital converter is provided to input 78 of a controller 80. The controller 80 may include circuitry including but not limited to a processor executing computer executable instructions, e.g., software, to perform the functions described herein.

In some embodiments, the controller 80 may be configured to orchestrate operation of one or more of the components within the dashed line 82. The controller 80 may be configured to send one or more commands to the first multiplexer 60a and second multiplexer 60b to select two or more conductors 30 in communication with one of the temperature sensors 16, in order to obtain a temperature reading from that temperature sensor 16. In some embodiments, the first multiplexer 60a and 60b are configured to provide an open circuit with respect to the unselected conductors 30 so that only a particular one of the temperature sensors 16 is read at any particular instant of time.

In some embodiments, temperature readings may be obtained by routing a known amount of electricity, e.g., current, through the at least two conductors 30 to the temperature sensor 16 (e.g., thermistor) and measuring an electrical reading, e.g., voltage, that appears across the temperature sensor 16. For example, a programmable current source 84 may be configured to generate a known current (e.g., 150 μA) through the at least two conductors 30. The first multiplexer 60a may be bidirectional such that the known current may be routed to the temperature sensor 16 via the selected conductors 30 by the first multiplexer 60a.

Figure 4A:
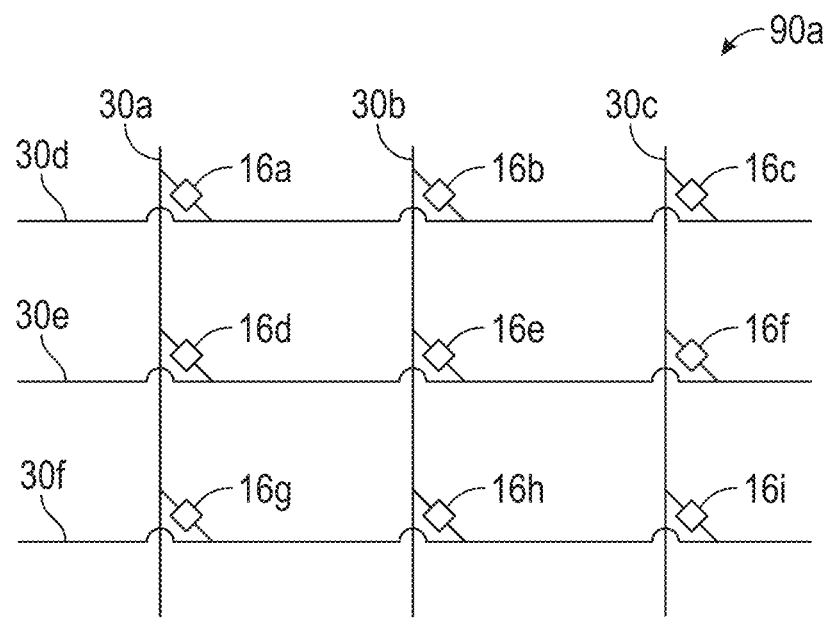
FIGS. 4A-4C illustrate schematic diagrams of exemplary embodiments of sensor arrays for use in the system illustrated in FIG. 1 in accordance with the present disclosure.

Referring to FIGS. 3 and 4A, temperature readings obtained from temperature sensors 16 within a sensor array 90a may be obtained using selective activation of at least two conductors 30. The controller 80 sends one or more commands to the first multiplexer 60a and the second multiplexer 60b to select at least two conductors 30a and 30d in communication with the first temperature sensor 16a within the sensor array 90a, and configures the current source 84 to generate a known current via the two conductors 30a and 30d.

The known current from the current source 84 is configured to flow through the first multiplexer 60a to the first temperature sensor 16a via the two conductors 30a and 30d connected to the first temperature sensor 16a resulting in a voltage appearing across the temperature sensor 16a and at the output 62a of the first multiplexer 60a. In some embodiments, the known current from the current source 84 is configured to flow through the first multiplexer 60a to the first temperature sensor 16a via the two conductors 30a and 30d connected to the first temperature sensor 16a resulting in a voltage appearing across the temperature sensor 16a and the output 62a of the first multiplexer 60a. The input 66 of the amplifier 68 receives the voltage appearing across the temperature sensor 16a, the amplifier 68 amplifies the voltage, and then provides the amplified voltage to the input 72 of the analog to digital converter 74. The controller 80 instructs the analog to digital converter 74 to digitize the resulting voltage. The controller 80 obtains the digitized resulting voltage reading from the analog to digital converter 74 and temporarily stores the digitized resulting voltage reading (which corresponds to the first temperature sensor 16a) in a buffer. The procedure may be repeated, sequentially, for each of the temperature sensors 16 within the sensor array 90a.

For example, to obtain a reading from the temperature sensor 16b, the controller 80 sends one or more commands to the first multiplexer 60a and the second multiplexer 60b to select the at least two conductors 30b and 30d in communication with the temperature sensor 16b, and configures the current source 84 to generate a known current to the at least two conductors 30b and 30d. The known current from the current source 84 is configured to flow through the first multiplexer 60a into the temperature sensor 16b via the conductor 30b and to the second multiplexer 60b via the conductor 30d resulting in a voltage appearing across that temperature sensor 16b and at the output 62 of the first multiplexer 60a. Similarly, to obtain a reading from the temperature sensor 16h, the controller 80 sends one or more commands to the first multiplexer 60a and the second multiplexer 60b to select the at least two conductors 30b and 30f in communication with the temperature sensor 16h, and configures the current source 84 to generate a known current. The known current from the current source 84 is configured to flow through the first multiplexer 60a into the temperature sensor 16h via the conductor 30b and to the second multiplexer 60b via the conductor 30f resulting in a voltage appearing across that temperature sensor 16h and at the output 62a of the multiplexer 60a.

Figure 4B:
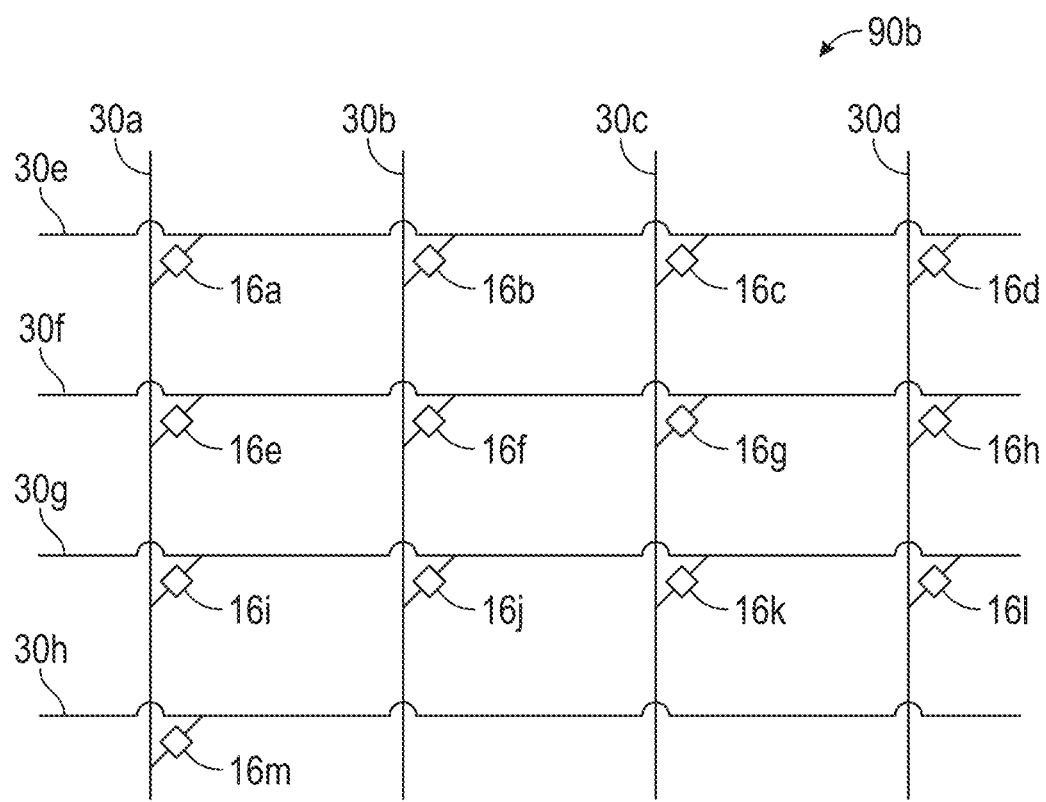
Figure 4C:
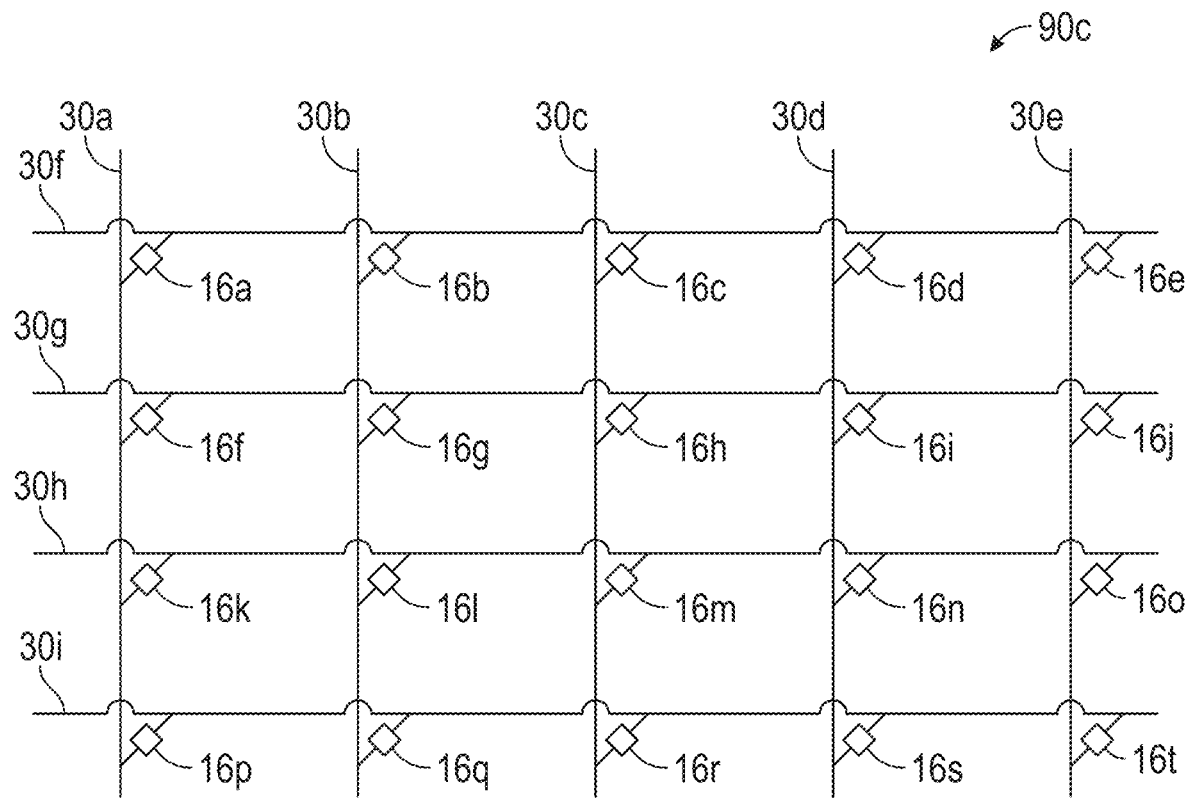

It should be understood that additional conductors 30 may be used to increase the number of temperature sensors 16 within the sensor array 90. For example, FIG. 4B illustrates another exemplary embodiment of a sensor array 90b having thirteen temperature sensors 16a-16m connected to conductors 30a-30h. Selective activation of at least two predetermined conductors 30 may result in a voltage appearing across at least one temperature sensor 16 connected to the at least two conductors 30 resulting in the temperature reading as described herein. FIG. 4C illustrates another exemplary embodiment of a sensor array 90c having twenty temperature sensors 16a-16u connected to conductors 30a-30t. Selective activation of at least two conductors 30 may result in a voltage appearing across the temperature sensor 16 connected to the at least two conductors 30 resulting in the temperature reading as described herein.

Figure 5:
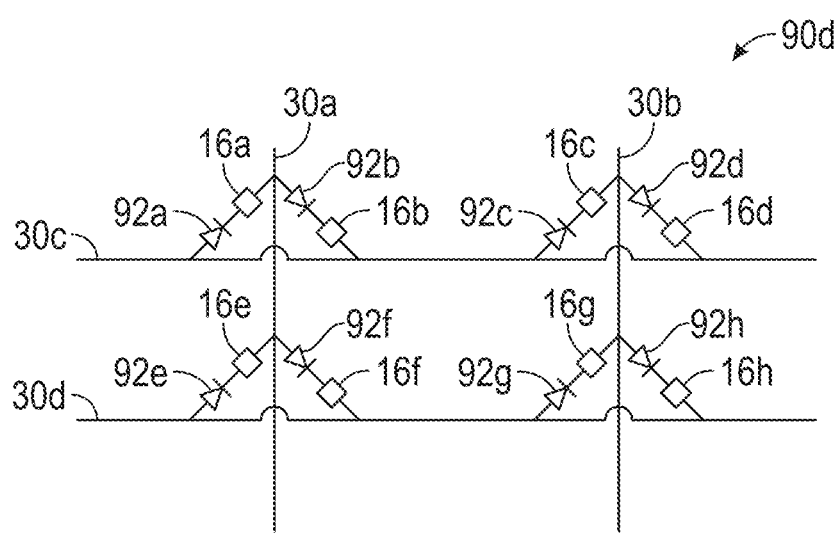
FIG. 5 is a schematic diagram of another exemplary embodiment of a sensor array for use in the system illustrated in FIG. 1 in accordance with the present disclosure.

FIG. 5 illustrates another exemplary embodiment of a sensor array 90d that includes a reduced number of conductors 30 relative to the embodiments of FIG. 4A-4C including a plurality of electronic switches 92, such as diodes configured to provide selective activation of one temperature sensor 16 when more than one temperature sensor 16 are connected to two conductors 30. In one embodiment, the selection of the temperature sensor 16 can be accomplished by providing a particular polarity of voltage across the two conductors 30. Generally, by providing a positive polarity or a negative polarity to a combination of conductors 30, particular temperature sensors 16 may be activated. For example, two temperature sensors 16g and 16h are connected in circuit with the two conductors 30b and 30d, and two electronic switches 92g and 92h. The electronic switch 92g is in series with the temperature sensor 16g; and the electronic switch 92h is in series with the temperature sensor 16h. The electronic switch 92g is configured to conduct based upon a negative polarity, and the electronic switch 92h is configured to conduct based upon a positive polarity. By applying a positive polarity across conductors 30b and 30d, temperature sensor 16h may be activated (and temperature sensor 16g is not activated) providing a temperature reading. By applying a negative polarity across the same conductors 30b and 30d, temperature sensor 16g may be activated (and temperature sensor 16h not activated) providing a temperature reading.

Referring to FIG. 3, in some embodiments, a conventional voltage divider approach for interfacing with the one or more temperature sensors 16 may be used. In some embodiments, additional readings may be obtained and used for self-calibration to increase the accuracy and/or precision of the temperature readings obtained from the one or more temperature sensors 16. For example, in FIG. 3, at least one input 64c of the first multiplexer 60a is connected to ground, and at least one input 64d of the first multiplexer 60a is connected to a precision resistor 100. The controller 80 may temporarily store the digitized readings from the precision resistor 100 and the grounded input 64c in a buffer and/or any memory configured to store data. These additional readings may ultimately be used to calibrate the readings that were obtained from the one or more temperature sensors 16. In some embodiments, such calibration may be implemented via the controller 80. In some embodiments, calibration may occur prior to transmission of the digital data that corresponds to the temperature readings. In some embodiments, calibration may be implemented in a downstream processor (e.g., the controller 40 in the hub 20) such that the digital data corresponding to the precision resistor 100 (and optionally the grounded input 64) may be transmitted to a downstream processor, in addition to, any uncalibrated temperature readings obtained from the one or more temperature sensor 16.

In some embodiments, calibration using the precision resistor 100 may compare the actual voltage measured across the precision resistor 100 with an expected voltage based on Ohm's law, the known value of the precision resistor 100, and the expected value of the current being produced by the current source 84. Deviations between the actual measured voltage and the expected voltage may be used to determine subsequent measurements (e.g., use as a multiplier) from the one or more temperature sensors 16.

In some embodiments, the controller 80 in the distal circuit 12 may be configured to communicate with the hub 20 via UART 102, and transmit the temperature readings obtained from the one or more temperature sensors 16 to the hub 20. In some embodiments, the controller 80 may be a processor programmed to operate autonomously and configured to automatically collect temperature readings from each of the one or more temperature sensors 16, storing the result in a buffer as described above, and subsequently transmitting contents of the buffer (i.e., readings for each of the temperature sensors 16, and optionally the additional readings described herein) to the hub 20.

In some embodiments, the controller 80 may be a processor programmed to operate as a slave to a master controller located in the hub 20. For example, the controller 80 may begin in a quiescent state, wherein the controller 80 solely monitors incoming commands from the master controller that arrive via the UART 102. Examples of commands that can arrive from the master controller may include, but are not limited to, "collect samples" command, "send data" command, and/or the like. When the controller 80 recognizes that a "collect samples" command has arrived, the controller 80 may be configured to initiate the method described herein to obtain one or more temperature readings from the one or more temperature sensors 16, and store results in the buffer and/or any memory configured to store data. In another example, the controller 80 may recognize a "send data" command, and execute a method to transmit previously collected temperature readings from the buffer and/or memory to the hub 20 via the UART 102.

In some embodiments, temperature measurements may be synchronized. For example, the controller 40 in the hub 20 may send a "collect samples" command to one or more controllers 80 in the distal circuit 12 either simultaneously or in rapid succession, such that the temperature readings obtained from each of the transducer arrays 14 may be obtained at or near the same time. In some embodiments, the temperature readings may be collected by the hub 20 in one or more batches of each controller 80.

Most systems that use TTFields to treat tumors switch the direction of the field that is being applied to the tumor periodically (e.g., every second). To minimize noise in the temperature measurements, a small time gap during which the field is not applied in either direction may be introduced, and the temperature measurements can be made during the time gap. In some embodiments, the controller 40 located in the hub 20 may synchronize timing of the "collect samples" command to all controllers 80 such that each of the distal circuits 12 may obtain temperature readings during the time gap. The temperature readings simultaneously obtained from each transducer arrays 14 may minimize duration of the time gap. For example, if the system 10 requires 100 µs to obtain a single measurement, taking thirty-six measurements in sequence (i.e., four distal circuits×nine temperature sensors 16 at each distal circuit 12, for example) may take 3.6 ms. In contrast, if each of four distal circuits 12 operates in parallel, each distal circuit 12 can obtain 9 samples in 900 µs, such that 36 samples can be obtained in 900 µs. It should be noted that the "send data" command may not be sensitive to noise such that the "send data" command can be executed while the fields remain on, and as such, is not time-critical.

In some embodiments, some or all of the following components may be implemented by a single integrated circuit: first multiplexer 60a, second multiplexer 60b, amplifier 68, analog to digital converter 74, controller 80, UART 102, and current source 84. One example of a single integrated circuit that includes all of these functional blocks is the Cypress CY8C4124LQI-443T programmable system on chip (PSoC), manufactured by Cypress Semiconductor Corp., having a principal place of business in San Jose, CA.

From the above description, it is clear that the inventive concepts disclosed and claimed herein are well adapted to carry out the objects and to attain the advantages mentioned herein, as well as those inherent in the invention. While exemplary embodiments of the inventive concepts have been described for purposes of this disclosure, it will be understood that numerous changes may be made which will readily suggest themselves to those skilled in the art and which are accomplished within the spirit of the inventive concepts disclosed and claimed herein.

What is claimed is:

1. An apparatus for imposing electric fields through a target region in a body of a patient, the apparatus comprising:
   at least one transducer array having a first electrode element and a second electrode element configured for placement on the body of the patient, the first electrode element and the second electrode element configured to provide TTFields via an alternating current waveform;
   a sensor array having a first temperature sensor positioned to detect a first temperature of the first electrode element, and a second temperature sensor positioned to detect a second temperature of the second electrode element, the first temperature sensor of the sensor array connected to a first conductor and a second conductor, and the second temperature sensor connected to the second conductor and a third conductor;
   a circuit configured to provide a first known amount of electricity via the first conductor and the second conductor to and obtain a first temperature reading of the first temperature sensor, and a second known amount of electricity via the second conductor and the third conductor to obtain a second temperature reading of the second temperature sensor; and a controller adjusting the alternating current waveform based on the first temperature reading.

2. The apparatus of claim 1, wherein the circuit further comprises:

a current source providing the first known amount of electricity;

a first multiplexer having an input and an output, the first multiplexer connected to the current source;

a second multiplexer having an input and an output, the second multiplexer connected to a reference point; and, a controller configured to send at least one command to the first multiplexer to select the first conductor and at least one command to the second multiplexer to select the second conductor to provide the first known amount of electricity via the first conductor and the second conductor to and obtain the first temperature reading of the first temperature sensor.

3. The apparatus of claim 2, wherein the controller is in communication with the current source and is configured to command the current source to generate the first known amount of electricity to the first conductor and the second conductor.

4. The apparatus of claim 2, wherein a first electrical reading corresponding to the first temperature sensor is obtained at the output of the first multiplexer.

5. The apparatus of claim 4, wherein the circuit further comprises an analog to digital converter configured to obtain the first electrical reading and provide a digitized resulting reading corresponding to the first temperature reading of the first temperature sensor.

6. The apparatus of claim 5, wherein the circuit further comprises a buffer configured to store the digitized resulting reading of the first temperature sensor.

7. The apparatus of claim 5, wherein the circuit further comprises an amplifier configured to receive the first electrical reading and provide an amplified voltage to the analog to digital converter.

8. The apparatus of claim 1, wherein the sensor array includes a first electronic switch coupled in series with the first temperature sensor, and a second electronic switch coupled in series with the second temperature sensor.

9. The apparatus of claim 8, wherein the first electronic switch is configured to conduct upon a first predetermined polarity being placed across the first electronic switch.

10. The apparatus of claim 9, wherein the second electronic switch being configured to conduct upon a second predetermined polarity being placed across the second electronic switch.

11. The apparatus of claim 10, wherein the first predetermined polarity is a negative polarity, and wherein the second predetermined polarity is a positive polarity.

12. An apparatus for imposing electric fields through a target region in a body of a patient, the apparatus comprising:

at least one transducer array having a plurality of electrode elements configured for placement on the body of the patient, the electrode elements configured to provide TTFields via an alternating current waveform;

a sensor array having a first circuit comprising a first temperature sensor coupled with a first electronic switch, a second circuit comprising a second temperature sensor coupled with a second electronic switch, a first conductor, and a second conductor, the first circuit coupled to the first conductor and the second conductor, the second circuit coupled to the first conductor and the second conductor, the first electronic switch configured to conduct electricity when a positive polarity of voltage is applied across the first conductor and the second conductor, the second electronic switch configured to conduct electricity when a negative polarity of voltage is applied across the first conductor and the second conductor; and a controller configured to:

provide the positive polarity of voltage to the first conductor and the second conductor for activation of the first temperature sensor via the first conductor and the second conductor and provide the negative polarity of voltage to the first conductor and the second conductor for activation of the second temperature sensor via the first conductor and the second conductor;

obtain a first electrical reading induced by the positive polarity of voltage and a second electrical reading induced by the negative polarity of voltage; and determine a first temperature reading based on the first electrical reading and a second temperature reading based on the second electrical reading; and wherein the alternating current waveform is adjusted based on the first temperature reading and the second temperature reading.

13. The apparatus of claim 12, wherein the first electronic switch is coupled in series with the first temperature sensor.

14. The apparatus of claim 13, wherein the second electronic switch is coupled in series with the second temperature sensor.

15. A method, comprising:

in a circuit having a first conductor, and a second conductor, with each of the first conductor and the second conductor connected to a first temperature sensor and a second temperature sensor of a sensor array, providing a positive polarity of voltage via the first conductor and the second conductor to activate the first temperature sensor of the sensor array, and a negative polarity of voltage via the first conduct and the second conductor to activate the second temperature sensor of the sensor array, the first temperature sensor positioned to detect a first temperature of a first electrode element, and the second temperature sensor positioned to detect a second temperature of a second electrode element, the first electrode element and the second electrode element configured for placement on a body of a patient, the first electrode element and the second electrode element configured to provide TTFields via an alternating current waveform;

obtaining a first temperature reading induced by activation of the first temperature sensor;

obtaining a second temperature reading induced by activation of the second temperature sensor; and, adjusting the alternating current waveform based on at least one of the first temperature reading and the second temperature reading.

16. The method of claim 15, wherein the step of adjusting the alternating current waveform is based on the second temperature reading.

* * * * *